(12) United States Patent
Jesse

(10) Patent No.: US 7,970,548 B2
(45) Date of Patent: Jun. 28, 2011

(54) AFLP-BASED METHOD FOR INTEGRATING PHYSICAL AND GENETIC MAPS

(75) Inventor: Taco Peter Jesse, Wageningen (NL)

(73) Assignee: Keygene N.V., Wageningen (NL)

( * ) Notice: Subject to any disclaimer, the term of this patent is extended or adjusted under 35 U.S.C. 154(b) by 1120 days.

(21) Appl. No.: 10/541,791

(22) PCT Filed: Jan. 9, 2004

(86) PCT No.: PCT/NL2004/000017
§ 371 (c)(1),
(2), (4) Date: Mar. 16, 2006

(87) PCT Pub. No.: WO2004/063323
PCT Pub. Date: Jul. 29, 2004

(65) Prior Publication Data
US 2006/0246445 A1    Nov. 2, 2006

(30) Foreign Application Priority Data
Jan. 10, 2003    (EP) .................................... 03075090

(51) Int. Cl.
*G01N 33/48* (2006.01)
*C12Q 1/68* (2006.01)
*G06G 7/58* (2006.01)

(52) U.S. Cl. .................. 702/19; 435/6; 702/20; 703/11

(58) Field of Classification Search ........................ None
See application file for complete search history.

(56) References Cited

OTHER PUBLICATIONS

Klein et al., Genome Research, vol. 10, pp. 789-807, 2000.*

* cited by examiner

*Primary Examiner* — Shubo (Joe) Zhou
(74) *Attorney, Agent, or Firm* — Browdy and Neimark, PLLC

(57) ABSTRACT

The invention pertains to a method for the integration of physical and genetic maps and markers. The method is based on the use of AFLP fingerprinting with primers of varying selectivity on a library of artificial chromosomes such as a BAC library. The fingerprinting is performed on the individual BACs and on the pools of BACs. Subsequent alignment generates a contig and provides the integration of physical and genetic markers resulting in the integration of the physical and genetic map.

20 Claims, 3 Drawing Sheets

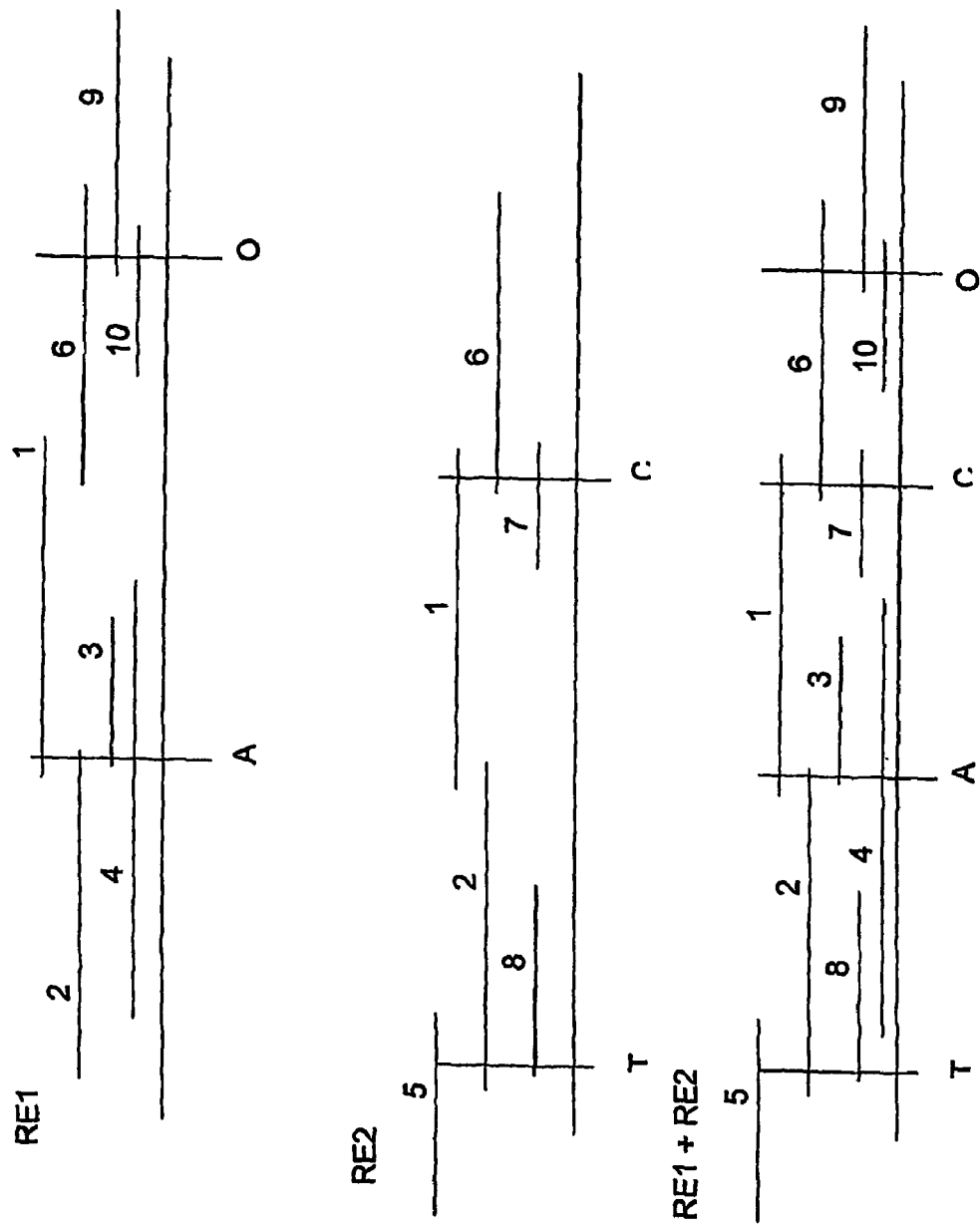

AFLP-BASED METHOD FOR INTEGRATING PHYSICAL AND GENETIC MAPS

FIELD OF THE INVENTION

The present invention pertains to the field of biotechnology, more in particular to the field of genomic mapping and more in particular to the field of linking physical and genetic markers and to the field of integrating physical and genetic maps. The invention pertains to a method for the integration of physical and genetic maps, more in particular to the high throughput building of integrated genetic and physical maps.

BACKGROUND OF THE INVENTION

Integrated genetic and physical genome maps are extremely valuable for map-based gene isolation, comparative genome analysis and as sources of sequence-ready clones for genome sequencing projects. The effect of the availability of an integrated map of physical and genetic markers of a species for genome research is enormous. Integrated maps allow for precise and rapid gene mapping and mapping of all microsatellite loci and other application such as SNA marker based gene manipulation. Various methods have been developed for assembling physical maps of genomes of varying complexity. One of the better characterised approaches use restriction enzymes to generate large numbers of DNA fragments from genomic subclones (Brenner et al., Proc. Natl. Acad. Sci., (1989), 86, 8902-8906; Gregory et al., Genome Res. (1997), 7, 1162-1168; Marra et al., Genome Res. (1997), 7, 1072-1084). These fingerprints are compared to identify related clones and to assemble overlapping clones in contigs. The utility of fingerprinting for ordering a complex genome is limited, however, due to variation in DNA migration from gel to gel, the presence of repetitive DNA sequences, unusual distribution of restriction sites and skewed clone representation. Moreover, fingerprinting alone, unless combined with other methods, does not link genomic clones directly to genetic maps. Therefor most high quality physical maps of complex genomes have been constructed using a combination of fingerprinting and PCR-based or hybridisation based methods.

Selective restriction fragment amplification or AFLP is known, for instance from the European patent application 0 534 858 and U.S. Pat. No. 6,045,994 by applicant and from an article by Vos et al. Nucleic Acids Research (1995), 23, 4407-4414, incorporated herein by reference. In general, AFLP comprises the steps of:
  (a) digesting a nucleic acid, in particular a DNA or a cDNA, with one or more specific restriction endonucleases, to fragment said DNA into a corresponding series of restriction fragments;
  (b) ligating the restriction fragments thus obtained with at least one double-stranded synthetic oligonucleotide adapter, one end of which is compatible with one or both of the ends of the restriction fragments, to thereby produce tagged restriction fragments of the starting DNA;
  (c) contacting said tagged restriction fragments under hybridising conditions with at least one oligonucleotide primer;
  (d) amplifying said tagged restriction fragments hybridised with said primers by PCR or a similar technique so as to cause further elongation of the hybridised primers along the restriction fragments of the starting DNA to which said primers hybridised; and
  (e) identifying or recovering the amplified or elongated DNA fragment thus obtained.

The amplified DNA-fragments thus obtained can then be analysed and/or visualised, for instance by means of gel-electrophoresis. This provides a genetic fingerprint showing specific bands corresponding to the restriction fragments which have been linked to the adapter, have been recognised by the primer, and thus have been amplified during the amplification step. The fingerprint thus obtained provides information on the specific restriction site pattern of the starting DNA, and thus on the genetic make-up of the organism from which said DNA has been derived.

AFLP can therefore be used to identify said DNA; to analyse it for the presence of specific restriction site patterns, restriction fragment length polymorphisms (RFLPs) and/or specific genetic markers (so-called "AFLP-markers"), which may be indicative of the presence of certain genes or genetic traits; or for similar purposes, for instance by comparing the results obtained to DNA-samples of known origin or restriction pattern, or data thereon. AFLP is eminently suited to characterise genetic markers by means of one or more of the AFLP fragments thus visualised.

The primers used in AFLP are such that they recognise the adapter and can serve as a starting point for the polymerase chain reaction. To this end, the primers must have a nucleotide sequence that can hybridise with (at least part of) the nucleotide sequence of the adapter adjacent to the 3' end of the restriction fragment to be amplified. The primers can also contain one or more further bases (called "selective bases") at the 3'-end of their sequence, for hybridisation with any complementary base or bases at the 3'-end of the adapter ligated restriction fragment. Located between the part of the primer that hybridises to the adapter and the selective bases that hybridise to the restriction fragment, the primer may contain a section that is capable of hybridising to the remains of the restriction site. Thus, in general an AFLP primer has the following structure: adapter complementary part-restriction site remains complementary part-selective bases. The adapter complementary part-restriction site remains complementary part is generally depicted as the 'constant sequence' of the AFLP primer and the selective bases as the 'variable sequence'.

As, of all the adapter-ligated restriction fragments present in the mixture, only those fragments that contain bases complementary to the selective bases will subsequently be amplified, the use of these "selective" primers will reduce the total amount of bands in the final fingerprint, thus making the fingerprint more clear and more specific. Also, the use of different selective primers (i.e. different variable sequence) will generally provide different fingerprints, which can also be used as a tool for the purposes of identification or analysis.

The selective nucleotides are complementary to the nucleotides in the adapter-ligated restriction fragments that are located adjacent to the constant primer sequence.

Primers containing selective nucleotide are denoted as +N primers, in which N stands for the number of selective nucleotides present at the 3'-end of the primer. N is preferably selected from amongst A, C, T or G.

N may also be selected from amongst various nucleotide alternatives, i.e. compounds that are capable of mimicking the behaviour of ACTG-nucleotides but in addition thereto have other characteristics such as the capability of improved hybridisation compared to the ACTG-nucleotides or the capability to modify the stability of the duplex resulting from the hybridisation. Examples thereof are peptide nucleic acids (PNAs), locked nucleic acids (LNAs), inosine etc. When the amplification is performed with more than one primer, such as with PCR using two primers, one or both primers can be equipped with selective nucleotides. The number of selective nucleotides may vary, depending on the species or on other particulars determinable by the skilled man. In general the number of selective nucleotides is not more than 10, but at least 5, preferably 4, more preferably 3, most preferred 2 and especially preferred is 1 selective nucleotide.

A +1 primer thus contains one selective nucleotide, a +2 primer contains 2 selective nucleotides etc. A primer with no selective nucleotides (i.e. a conventional primer) can be depicted as a +0 primer (no selective nucleotides added). When a specific selective nucleotide is added, this is depicted by the notion +A or +C etc.

By amplifying a set adapter ligated restriction fragments with a selective primer, a subset of adapter-ligated restriction fragments is obtained, provided that the complementary base is present at the appropriate position in the restriction fragment. Using a +1 primer, for example, the complexity (and the number of visualised fragments) of the amplified mixture is reduced by a factor 4 compared to a amplification with a non-selective primer (a+0 primer) Higher reductions can be achieved by using primers with multiple selective nucleotides, i.e. 16 fold reduction of the original multiplex ration is obtained with 2 selective nucleotides etc.

As AFLP provides amplification of both strands of a double stranded starting DNA, AFLP advantageously allows for exponential amplification of the fragment, i.e. according to the series 2, 4, 8, 16, etc. Also, AFLP requires no prior knowledge of the DNA sequence to be analysed, nor prior identification of suitable probes and/or the construction of a gene library from the starting DNA.

For a further description of AFLP, its advantages, its embodiments, as well as the techniques, enzymes, adapters, primers and further compounds and tools used therein, reference is made to EP-0 534 858, and to Vos et al. Nucleic Acids Research (1995), 23, 4407-4414 both publications are incorporated herein by reference. Also, in the description hereinbelow, the definitions given in paragraph 5.1 of EP-0 534 858 will be used, unless indicated otherwise.

The potential of AFLP as a technology for the integration of physical and genetic maps has been recognised before. Klein et al. in Genome Research, (2000), 10, 798-807 have described the use of AFLP in the integration of physical and genetic maps of *Sorghum*. The method of Klein et al. comprises generating AFLP fingerprints using +3/+3 selective primers of all individual BAC clones in a library. The method further comprises the generation of pools of clones. The pools are also analysed by AFLP fingerprinting albeit using different restriction enzymes and otherwise other circumstances compared to the generation of the AFLP fingerprints of all the individual BACs. The use of different enzyme combinations renders the method difficult. The method of Klein et al. although feasible, is complex and laborious and comes with several other disadvantages. One of them is that the method is unsuitable for positioning non-polymorphic markers on the integrated map.

It is a goal of the present invention to provide for an improved method for the integration of physical and genetic maps. It is a further goal of the present invention to provide for an improved method based on AFLP. It is yet a further goal of the invention to provide for a high throughput method for the integration of physical and genetic maps that results in maps of improved quality such as measured by increased marker densities or as a result of more reliable contig generation.

DESCRIPTION OF THE INVENTION

The present invention pertains to methods for the integration of physical and genetic markers and for the integration of physical and genetic maps. The present invention overcomes many of the previously encountered problems in the art and provides for significant improvements and advantages that will become clear through this description, the claims and the examples. The method is based on AFLP and more in particular based on the use of combinations of selective primers in AFLP. The method results in the integration of genetic and physical maps and the linking of physical and genetic markers. The invention further pertains to the use of AFLP primers in the methods of the invention and to a set of structurally defined AFLP primers.

DETAILED DESCRIPTION OF THE INVENTION

In one aspect the invention pertains to a method for the integration of physical and genetic maps by associating a restriction fragment, preferably an AFLP fragment with a genetic marker, providing a library of clones containing inserts of the (part of) genome of interest, pooling the clones into pools and fingerprinting the pools using AFLP primer-pairs of higher selectivity, individually fingerprinting the clones in a library using AFLP primer-pairs of lower selectivity. The pools that contain a fragment corresponding to the fragment associated with the genetic marker are identified and the individual clones containing the fragment corresponding to the fragment associated with the genetic marker are identified and linked. From the fingerprint patterns of the individual clones containing the fragment associated with the genetic marker a contig is generated. The contig is linked to the genetic marker on the genetic map and the process is repeated for all genetic markers, thereby providing an integrated physical and genetic map.

The notion 'primer-pairs of higher/lower selectivity' as used herein relates to the number of selective nucleotides in the AFLP primers used for fingerprinting. Thus a +0/+0 primer-pair is of a lower selectivity than a +0/+1 primer-pair or a +1/+0 primer-pair. Similarly a +3/+4 primer-pair is of a higher selectivity than a +2/+2 primer-pair etc.

In one aspect the invention pertains to a method for linking a genetic and a physical genome map comprising the steps of:
(a) providing individual genetic markers, preferably in the form of a genetic map;
(b) characterising each of the genetic markers by means of at least one AFLP fragment identified through AFLP fingerprinting;
(c) providing an artificial chromosome library such as a BAC or YAC;
(d) generating a multitude of pools, each pool containing a multitude of artificial chromosomes from the library;
(e) generating an AFLP fingerprint for each of the pools;
(f) selecting from the multitude of pools the individual pools in which the at least one AFLP fragment associated with a genetic marker is present in the fingerprint of the individual pool;
(g) generating an AFLP fingerprint of the individual artificial chromosomes from the pools identified under (f);
(h) selecting from the fingerprints of the individual artificial chromosomes of step (g) the individual artificial chromosome(s) in which the AFLP fragment associated with the genetic marker is present in the fingerprint;
(i) generating a contig of the individual artificial chromosomes identified in step (h);
(j) linking the contig obtained in step (i) to the genetic marker on the genetic map, thereby obtaining a linkage between the physical marker and the genetic marker;

(k) repeating steps (g-j) for all genetic markers and align the contigs obtained to thereby obtain an integrated physical and genetic map;

wherein the forward and reverse AFLP primers used in step (b) and (f) comprise K respectively L selective nucleotides at the 3'-end of the primer, wherein the forward and reverse AFLP primers used in step (d) comprise M respectively N selective nucleotides at the 3'-end of the primer, wherein K, L, M, N are integers from 0 to 10, and wherein K+L≧M+N.

The method of the invention is flexible. Flexibility in this respect refers to the starting material. The method of the invention may start from whole genomes of any species, but is also applicable to only a part of the genome or a selected region of the genome or a chromosome or part thereof.

The method starts by using individual genetic markers. It is preferred that these markers have been integrated on a genetic map, but this is not a pre-requisite. The method of the inventions is equally well suited to link physical markers to genetic markers, after which the physical markers are aligned to from a physical map and at the same time provide a genetic map. The genetic map may comprise only one single genetic marker but preferably the map comprises two or more genetic markers. Each of the genetic markers is characterised by an AFLP fragment or by a combination of AFLP fragments. The second step is the provision of a library of artificial chromosomes. The library can be a Bacterial Artificial Chromosome library (BAC) or based on Yeast Artificial Chromosome (YAC). Other libraries such as based on Cosmids, PAC, TAC or MAC are also possible. Preferred is a BAC library. The library is preferably of a high quality and preferably is a high insert size genomic library. This means that the individual BAC contains a large insert of the genomic DNA under investigation. The size of the preferred large insert is species-dependent. Throughout this application reference is made to BACs as examples of artificial chromosomes. However, it is noted that the present invention is not limited thereto and that other artificial chromosomes can be used without departing from the gist of the invention. Preferably the libraries contain at least five genome equivalents, more preferably at least 7, most preferably at least 8. Particularly preferred is at least 10. The higher the number of genome equivalents in the library the more reliable is the resulting contig and the integrated maps.

The individual clones in the library are pooled to form pools containing a multitude of artificial chromosomes or clones. The pooling may be the simple combination of a number of individual clones into one sample (for example, 100 clones into 10 pools of 10 clones), but also more elaborate pooling strategies may be used. The distribution of the clones over the pools is preferably such that each clone is present in at least two or more of the pools. The pools are generated based on pooling strategies well known in the art. The skilled man is capable selecting the optimal pooling strategy based on factors such as genome size etc. The resulting pooling strategy will depend on the circumstances, and examples thereof are plate pooling N-dimensional pooling such as 3D-pooling, 6D-pooling or complex pooling.

Each of the pools is fingerprinted using AFLP and preferably with primer-pairs having a high selectivity to thereby generate fingerprints that contain a limited number of bands or fragments. Preferably the primer-pairs used in the finger-printing of the pools are the same primer-pairs that are used to identify the AFLP fragment characteristic of the genetic markers in step (b). The primer-pairs with a high selectivity contain more selective nucleotides than the primer with a low selectivity and are for instance +3/+3 primer-pairs or +2/+3 primer-pairs.

The fingerprints of the pools are subsequently screened for the presence or absence of the fragments of interest that are associated with the genetic marker(s). From a pool (or pools) in which the desired fragment has been found present, each of the individual clones in that pool (or pools) is fingerprinted using AFLP. The individual clones are preferably finger-printed with primer-pairs having a low selectivity to thereby generate fingerprints that contain a large number of bands or fragments that later aid in the generation of reliable contigs. In general in this method, the AFLP fingerprints of the genetic markers, the pools and the individual clones are preferably obtained using the same combinations of enzyme(s) and adapters. Preferably only the primers are different and preferably only the selective bases are different in number and/or in type. The primer-pairs with a low selectivity are for instance +0/+0 primer-pairs or +1/+0 primer-pairs.

The fingerprints of the individual clones that have been obtained are now subjected to a selection step whereby those fragments are selected that are most likely connected to the genetic marker of interest. This is achieved by subjecting the individual clones containing the desired fragment to a selection step, preferably in silico.

In this selection step, the fingerprinting patterns of the individual clones are compared. When fingerprinting patterns are compared that are derived from clones with overlapping inserts, the respective fingerprints will contain one or more bands/fragments that are similar in place, intensity, type etc. (See for example FIG. 1., the bands are marked as #,^$). With fingerprint patterns that are derived from clones that do not have overlapping inserts the chance that one or more bands express such a similarity is significantly lower. When, based on the fingerprint patterns, it is likely that the associated inserts of the clones are overlapping inserts, alignment in silico results in the generation of a contig. This contig is then linked to the genetic marker and the genetic marker can be positioned on the genetic map. Repeating these steps for various genetic markers ultimately results in positioning of all contigs on the genetic map and in the integration of the physical and genetic map.

The advantage of the fingerprinting of the clones using primers with low selectivity is that many fragments are amplified. Consequently, a large number of physical markers are identified. Typically 4-5 times more scorable fragments are generated with a +0/+) amplification compared to +2/+3 amplification and leads consequently to a 4 or 5 times higher resolution of the contigged clones. In this way, a high-resolution physical map is generated. This is advantageously in the generation of contigs and it will reduce the number of singletons that may occur in the generation of contigs.

The term 'contig' as used herein refers to a continuous sequence of DNA that has been assembled from overlapping cloned DNA fragments, following the definition provided in *The Encyclopedia of Molecular Biology* (1994, Blackwell).

In general, the primers of low and high selectivity are characterised in that the forward and reverse AFLP primers of high selectivity used in the fingerprinting of the individual clones and in the identification of the AFLP fragment associated with the genetic marker comprise K respectively L selective nucleotides at the 3'-end of the primer, wherein the forward and reverse AFLP primers used in the fingerprinting of the individual clones from the library comprise M respectively N selective nucleotides at the 3'-end of the primer, wherein K, L, M, N are integers from 0 to 10, and wherein K+L≧M+N. Thus the primers of high selectivity contain at least one selective nucleotide more than the primers of low selectivity.

Alignment is performed by comparing band patterns and intensities of the fingerprint to identify overlapping patterns. Clones containing overlapping patterns overlap can be aligned based thereon. Due to the use of AFLP with low selective primers, the physical markers present in the clones are abundant and hence the alignment thereof can be performed with great accuracy. The contig can be generated using any means known in the art. The clones can be aligned using software well known in the art for these purposes such as FPC (Soderlund C., I. Longden, R. Mott, 1997, FPC: a system for building contigs from restriction fingerprinted clones. Comput. Applic. Biosci. 13:523-535). This software can be used in the method of the present invention with cut-off parameters that are between $10^{-5}$-$10^{-15}$, preferably between $10^{-6}$-$10^{-14}$, more preferably between $10^{-7}$-$10^{-13}$, in particular between $10^{-8}$-$10^{-12}$, more preferably between $10^{-9}$-$10^{-11}$, and most preferred $10^{-10}$. Cut-off is a parameter that that represents the threshold value representing the maximum allowable probability of a chance match between any two clones. Tolerance is a parameter that is a measure for the maximum distance or bandwidth which two bands from two different clones can differ and still be considered the same band. In this invention, tolerance is rated from 0 (identical) to 5 (difference of 0.5 base pair). Preferably, tolerance is as low as possible (i.e. 0), but in practice a value of 3-4 (difference of 0.3-0.4 base pair) is acceptable and 1-2 is preferred.

The generated contigs are then linked to the genetic marker on the genetic map and the whole process is repeated for the other genetic markers of the genetic map thereby integrating the genetic map with the physical map.

The method according to the invention has certain advantages over methods disclosed in the art. One of the advantages is that the resulting integrated map has high resolution due to the fingerprinting of the individual clones with primer-pairs of low selectivity. The amplification step of AFLP with low selective primers will result in the amplification of more adapter-ligated restriction fragments and consequently to more physical markers per clone as compared to similar fingerprinting with primers of high selectivity. Due to this increased number of physical markers per clone the subsequent generation of a contig is also of a better quality and more clones can be correctly aligned resulting in an improved integration of the physical and genetic map.

Another advantage is in the speed of the generation of the contig. With the method of the present invention relative small sets of individual clones are selected that are associated with the AFLP fragment of the genetic marker of which a contig is generated. Small sets have the advantage that the generation of a contig is significantly faster than when larger sets are used. After placement of the contigs in the genetic map, a more reliable integrated map is obtained by aligning the placed contigs and verifying the alignments with the position of the genetic marker on the genetic map. One of the further advantages is that the relative genetic distance (generally in centimorgan) are now converted to physical distances (in basepairs) and may provide a correction or enhancement of the genetic map, for instance by reversing the order of genetic markers or by more accurately determining the distance between markers. One of the most distinct advantages is that each step is verifiable and correctable. This means that in case an amplification or a detection, for instance on a gel, is not of the desired quality, this step can be immediately corrected until data of the desired quality are obtained.

A significant advantage of the method of the invention over the methods known in the art is that the present method provides for the detection of non-polymorphic markers and their subsequent integration in the integrated map. Another advantage associated with the method of the invention is that the generation of physical mapping data and linkage to the genetic map are achieved directly from the start of the method (for each marker separately).

In one embodiment the method can also be used for the linking or integrating of a physical and genetic marker. The method then comprises the steps of:
  (a) characterising the genetic marker by means of at least one AFLP fragment identified through AFLP fingerprinting;
  (b) providing an artificial chromosome library such as a BAC or YAC;
  (c) generating a multitude of pools, each pool containing a multitude of artificial chromosomes from the library;
  (d) generating an AFLP fingerprint for each of the pools;
  (f) selecting from the multitude of pools those individual pools in which the AFLP fragment associated with the genetic marker is present in the fingerprint of the individual pool;
  (g) generating an AFLP fingerprint of the individual artificial chromosomes from the pools identified under (f);
  (h) selecting from the fingerprints of the individual artificial chromosomes of step (g) the individual artificial chromosomes in which the AFLP fragment associated with the genetic marker is present in the fingerprint;
  (i) generating a contig of the individual artificial chromosomes identified in step (h);
  (j) linking the contig obtained in step (i) to the genetic marker on the genetic map thereby obtaining a linkage between the physical marker and the genetic marker;
wherein the forward and reverse AFLP primers used in step (b) and (f) comprise K respectively L selective nucleotides at the 3'-end of the primer, wherein the forward and reverse AFLP primers used in step d comprise M respectively N selective nucleotides at the 3'-end of the primer, wherein K, L, M, N are integers from 0 to 10, and wherein $K+L \geq M+N$.

In this embodiment the present invention is used for the single integration of a genetic marker with a (group of) physical marker(s). By repeating these steps for all available genetic markers, the complete integrated map can be constructed, but in this embodiment this is entirely optional.

In one embodiment, the difference in the number of nucleotides that are used in the set of primers with low selectivity compared to the set of primers of high selectivity, also depicted as (K+L)−(M+N), is at least 1, preferably at least 2, more preferably at least 3, most preferably at least 4. In one embodiment, the number of selective nucleotides used in the set of primers of low selectivity, also depicted as is M+N, is at least 0, preferably at least 1, more preferably at least 2, most preferably at least 3.

The pools of the individual clones that are used in the method of the present invention preferably contain between 0.001 and 1 genome equivalent of the total genome to be analysed, preferably between 0.1 and 0.75, more preferably between 0.15 and 0.60, most preferably between 0.20 and 0.50. More preferred is between 0.25 and 0.35, more preferably 0,4, most preferably 0.3.

In general, a pool of individual clones is limited in the number of clones it can contain. In case of exceptionally large genomes, libraries or very small inserts, it may be advantageously to introduce and additional pooling step. Therefore in a preferred embodiment of the invention, the method comprises an additional pooling step. The additional pooling step results in pools that can be fingerprinted using primers with the same (high) selectivity as are used for the fingerprinting of the pools of the initial pooling step. It is also possible to use primers of a intermediate selectivity, that is, primers with a number of selective nucleotides (P+Q) between K+L and M+N such that K+L≧P+Q≧M+N.

In an alternative embodiment, it is possible to avoid the use of pools of clones altogether by generating a contig of all individual clones that have been fingerprinted using primers with low selectivity. Optionally a pre-selection of the individual clones is made wherein the clones at least contain the fragment that is associated with the genetic marker. More in detail: the individual fingerprints obtained using primers of low selectivity are screened for the presence of the (fragment) marker associated with the genetic marker that has been identified using the primers with high selectivity. This embodiment is advantageously for instance when smaller genomes are investigated or when only a few genetic markers are integrated with the physical markers. In such cases there is no real need for a pooling step.

In one embodiment to characterise all genetic markers available by AFLP it may be preferred to use different primers and/or primer combinations for different genetic markers. The primers and/or primer combinations for the fingerprinting of the pools and the individual clones can then to be adapted accordingly. It is even possible to use different enzyme combinations for different genetic markers. The associated contigs of BACs can be aligned based on the overlap of the BAC contigs and the occurrence of identical physical markers. This is schematically depicted in FIG. 3.

The method of the invention is in principle suitable for the linkage of one or more physical markers to a genetic marker and for the linkage of physical markers to the genetic map comprising a multitude of genetic markers. It is preferred that the genetic markers are spread evenly across the map. It is further preferred that the genetic map is a map that is regarded in the art as a genetic map with a high marker density. This facilitates the linkage of (the contigs of) the physical markers to the genetic map and enhances the quality and reliability of the resulting integrated physical and genetic map. Preferably the genetic map has an (average) density of at least 1 genetic marker per 1000 kb, preferably per 500 kb more preferably per 200 kb, most preferably per 100 kb. Particularly preferred is a genetic map with a density of at least 1 genetic marker per 50 kb.

When all genetic markers are linked to a contig derived from the individual clones in the library, gaps may remain and/or clones may remain that have not been placed on the map. Due to the increased density of the physical markers obtained by the fingerprinting of the individual clones with primers of low selectivity, the placement of these clones can be accomplished using conventional alignment software, and using techniques such as BAC walking and using the BAC end sequences.

In another aspect, the present invention pertains to the use of AFLP primers for the integration of genetic and physical maps and to the use of AFLP and AFLP primers in linking genetic and physical genome maps. AFLP and AFLP primers have demonstrated to provide an excellent technique for the integration of the physical and genetic maps.

In a further aspect the invention pertains to the use of a first and a second pair of AFLP primers in a method for linking genetic and physical genome maps wherein the first pair of AFLP primers comprise K respectively L selective nucleotides at the 3'-end of the primer, wherein the second pair of AFLP primers used comprise M respectively N selective nucleotides at the 3'-end of the primer, wherein K, L, M, N are integers from 0 to 10, and wherein K+L≧M+N.

By linking the physical contigs to the genetic markers a first integrated map can be obtained. Based thereon further improvement, correction and refinement of the genetic map is possible by generating a contig of the various physical markers linked to a genetic marker.

The invention provides for the construction of high resolution integrated genetic and physical map of any genome without the need for prior knowledge of the sequence. The invention further facilitates the efficient construction of detailed physical maps of, optionally pre-selected, regions of any genome. The invention further facilitates the discovery of novel BAC derived (AFLP) markers, both polymorphic and non-polymorphic for the integrated genetic map.

DESCRIPTION OF THE FIGURES

FIG. 3: Schematic representation of the method for the integration of physical and genetic maps, whereby for different genetic markers the linkage between the physical BAC clones and the respective genetic markers is obtained by fingerprinting the BAC pools and the individual fingerprints with different restriction enzyme combinations in the AFLP fingerprinting for the different genetic markers. A, B and C are genetic markers. RE1 and RE2 are different restriction enzyme combinations (for instance HindIII/MseI and EcoRI/MseI). 1-8 are BAC clones.

Figure 1:
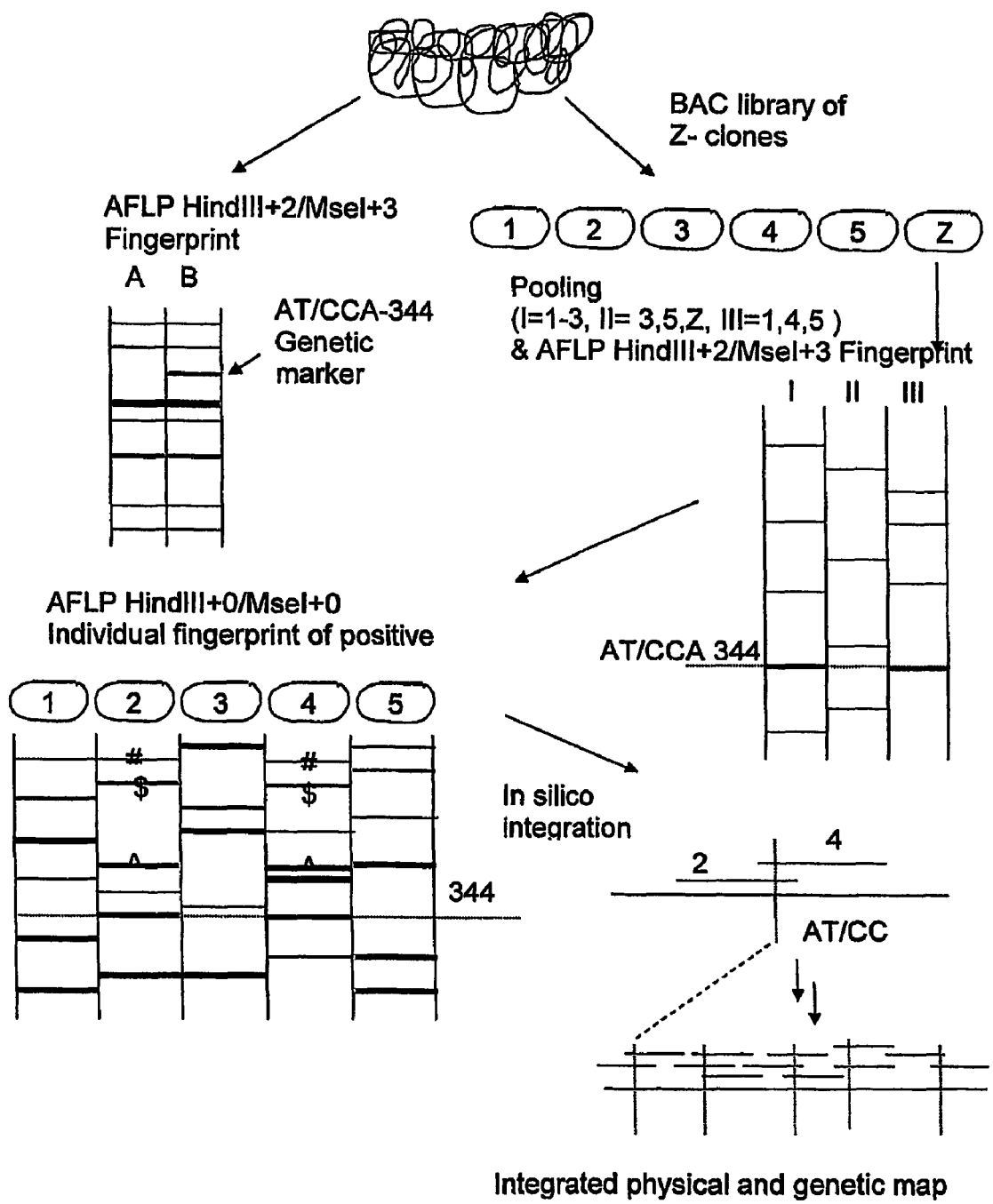
FIG. 1 discloses a schematic representation of the integration of a physical and a genetic map. The method starts by identifying genetic markers using AFLP fingerprinting. In this case a genetic marker was identified using HindIII and MseI as restriction endonucleases in the AFLP fingerprinting and Hind+2 and Mse+3 high selective primers carrying AT and CCA as selective nucleotides at their 3' end, respectively. The identified AFLP fragment associated with the genetic marker has a length of 344 bp. A BAC library is prepared comprising Z clones. The individual clones are pooled (pool I contains clones 1, 2 and 3; II contains 3, 5 and Z; and III contains 1,4, and 5) and the pools are fingerprinted using AFLP with identical enzymes and primers with the same selectivity as used in the identification of the genetic marker (Hind+2(AT) and Mse+3(CCA)). This positively identifies those pools that contain the fragment AT/CCA-344 (pools I and III). From each clone present in the pool (pools I and III) that contains the fragment of interest, (1, 2, 3, 4, 5) an AFLP fingerprint is generated, using primers of lower selectivity, in this case +0/+0. Each of the individual clones is fingerprinted and bands with 344 bp length can be identified (in 2, 3, 4, 5). These bands may very well be unrelated to the genetic marker of interest, as they also include any fragment that contains other nucleotides than the AT/CCA combination at the respective ends. From the individual fingerprints containing the 344 fragment the clones are selected in silico that are most likely to be linked to the AFLP fragment of interest. This selection step is based on the comparison of one or more bands in the fingerprint patterns. The more corresponding bands are found in the fingerprints (the bands are depicted as #,`$), the higher the likelihood that these fingerprints are able to form a contig and thus align the individual clones from the library to form a contig. The individual clones that contain a fragment with a length of 344 bp and that are selected based on the in silico process of the fingerprint patterns are aligned using FPC to form a contig. This contig can be placed on the genetic map. False positive fragments (i.e. that contain the fragment AT/CCA-344, but are not linked to the genetic marker of interest) will not form a contig under the conditions used. Repeating these steps for other genetic markers results in the formation of an integrated physical and genetic map.
Figure 2:
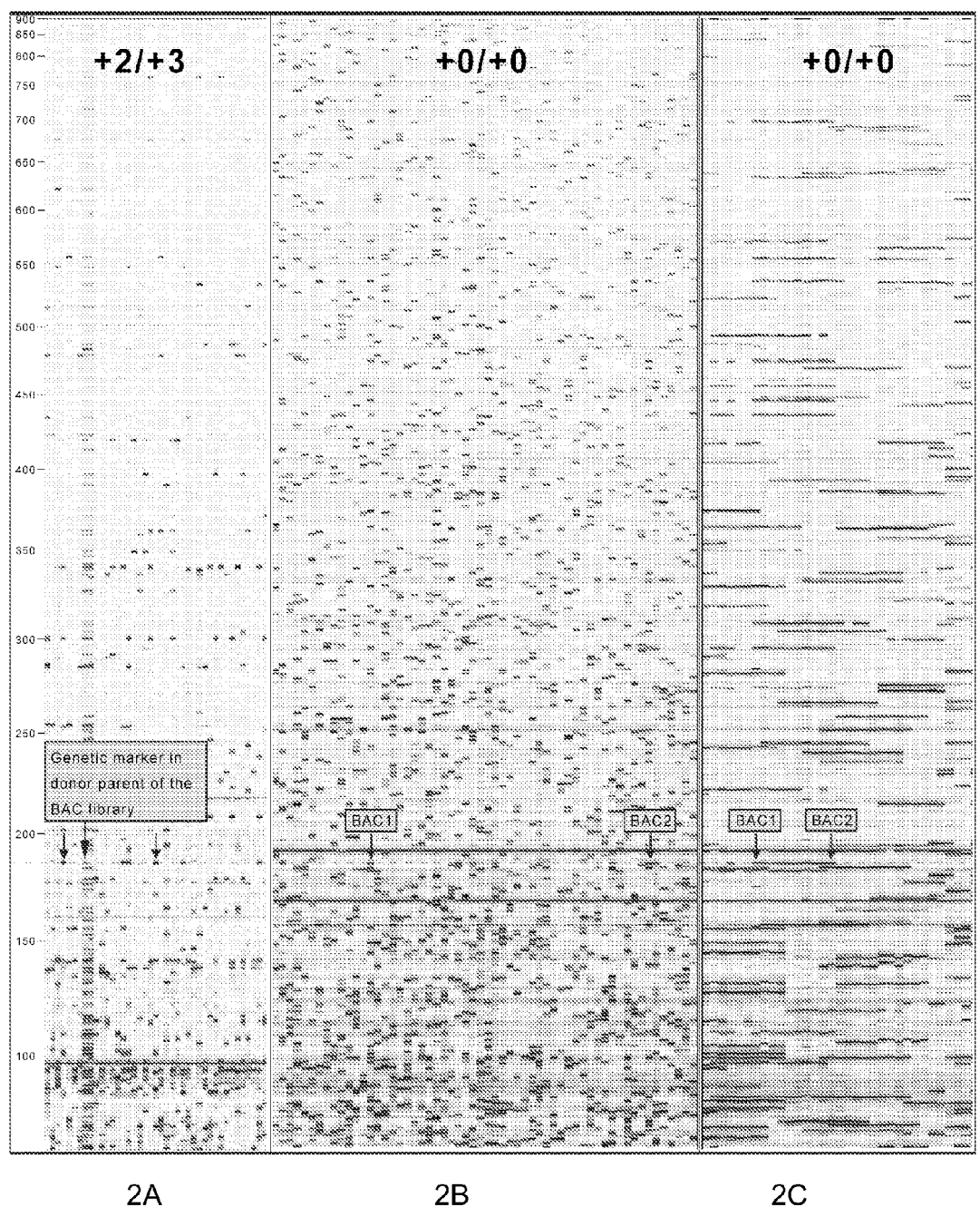
FIG. 2: A: HindIII+2/MseI+3 fingerprints of BAC pools of *Pristionchus pacificus* with the previously identified AFLP fragments characteristic of the genetic markers indicated by arrows.
B: HindIII+0/MseI+0 fingerprints of individual BACs of corresponding positive pools in FIG. 2A. and indication of the characteristic AFLP bands (BAC1 and BAC2).
C: Corresponding HindIII+0/MseI+0 BAC contig and identification of the BAC1 and BAC2 clones.

A genetic marker A has been linked to physical BAC clones 1-4 using enzyme combination RE1 in the AFLP fingerprinting of the donorparents, the BAC pools and the individual BACs according to the method of the invention. Genetic marker 0 has been mapped to BC clones 6, 9 and 10 using the same enzyme combination RE1. Genetic markers T and C have similarly been mapped to BAC clones 2,5, 8 and 1,6,7 respectively, using enzyme combination RE2. Based on the common presence of BAC clones 1 and 2 in A and in B and C respectively, the genetic marker A identified with a different enzyme combination than genetic markers B and C can now be placed on the common integrated map. Based on the common presence of BAC clone 6 in O and C respectively, genetic marker T can be located adjacent to genetic marker C on the integrated map, thereby providing for an integrated map of genetic markers T, A, C and O that have been identified using different AFLP enzyme combinations.

EXAMPLES

BAC Library Construction

High molecular weight DNA of the nematode *Pristionchus pacificus* was used to construct a BAC library. Partially HindIII digested DNA of *Pristionchus pacificus* was separated with pulsed field gel electrophoresis and ligated into the pIndigoBAC-536 vector. The ligated products were electroporated into electrocompetent DH10B *E. coli* cells and the average insert size was determined on field inversion gel electrophoresis. The *Pristionchus pacificus* BAC library contains 13.500 clones with an all over average insert size of >125 kb. The estimated genome coverage of the library is estimated to be at least 7 x, assuming a 200 Mb total genome size of *Pristionchus pacificus*.

The Pooling of the BAC Library

The pooling of the BAC library was performed by pooling individual 96-well plates. Each 96-well plate was inoculated on a standard TY-agarplate with chloroamphenicol selection (12.5 mg/ltr), and incubated overnight at 37 Celsius. In the morning the 96 colonies were resuspended in 1 ml of liquid TY medium and collected from the agarplates. A standard miniprep procedure was performed and the pooled BAC DNA was used for AFLP template preparation.

DNA Preparation of Individual BACs and BAC Pools

DNA from individual BACs was prepared according to standard procedures (Sambrook, J., Fritsch, E. F., and Maniatis, T., in Molecular Cloning: A Laboratory Manual. Cold Spring Harbor Laboratory Press, NY, Vol. 1, 2, 3 (1989).) An overnight 1.5 ml culture in TY medium and chloroamphenicol (12.5 mg/ltr) selection generates sufficient DNA for AFLP template preparation.

AFLP Analysis of Individual BACs and BAC Pools

AFLP templates of individual BAC DNA, the BAC pools and the two donorparents that were used in the genetic mapping population were prepared according to standard procedures (Vos et al. Nucleic Acids Research (1995), 23, 4407-4414) using HindIII and MseI as the enzyme combination.

For the +0/+0 amplification of the individual BAC fragments, no preamplification step was necessary. The +0/+0 amplification step was directly performed on the 1:10 diluted template of the individual BAC DNA. The amplified +0/+0 fragments were detected and sized on a MegaBACE 1000 capillary electrophoresis platform.

AFLP reactions on the BAC pools were preceded by +1/+1 preamplifications with one selective nucleotide on each primer. AFLP reactions were performed with primer combinations having 2 selective nucleotides on the HindIII primer and 3 selective nucleotides on the MseI primer.

The amplified +2/+3 AFLP fragments were detected and sized on the same MegaBACE 1000 capillary electrophoresis platform as the +0/+0 fingerprints.

AFLP Adaptor Primers (5'-3')

The following primers were used to generate the fingerprints of the BAC clones

```
91M35:   HindE-adaptor primer   CTCGTAGACTGCGTACC
         forward (5'-3'):       (SEQ ID NO: 1)

91M37:   HindE-adaptor primer   AGCTGGTACGCAGTCTAC
         reverse (5'-3'):       (SEQ ID NO: 2)

92A18:   MseI-adaptor primer    GACGATGAGTCCTGAG
         forward (5'-3'):       (SEQ ID NO: 3)

92A19:   MseI-adaptor primer    TACTCAGGACTCAT
         reverse (5'-3'):       (SEQ ID NO: 4)
```

Non Selective Primer Sequences (4'-3')

```
93Q34:   Hindi+0 primer (5'-3'):   GACTGCGTAC-
                                   CAGCTT
                                   (SEQ ID NO: 5)

93E40:   MseI+0 primer (5'-3'):    GATGAGTCCTGAGTAA
                                   (SEQ ID NO: 6)
```

AFLP Selective Primer Sequences (5'-3')

HindIII+2 primers can be labeled with FAM, JOE or NED for detection on MegaBACE platform.

```
HindIII + 2 primers (5'-3'):

Constant sequence: GACTGCGTACCAGCTT
(SEQ ID NO: 7)

Selective nucleotides:    AA    CA    GA    TA
                          AC    CC    GC    TC
                          AG    CG    GG    TG
                          AT    CT    GT    TT MseI + 3 primers (5'-3'):

Constant sequence: GATGAGTCCTGAGTAA (SEQ ID NO: 8)

Selective nucleotides:
AAA   TAA   CAA   GAA   AGA   TGA   CGA   GGA
AAC   TAC   CAC   GAC   AGC   TGC   CGC   GGC
AAT   TAT   CAT   GAT   AGT   TGT   CGT   GGT
AAG   TAG   CAG   GAG   AGG   TGG   CGG   GGG
ACA   TCA   CCA   GCA   ATA   TTA   CTA   GTA
ACC   TCC   CCC   GCC   ATC   TTC   CTC   GTC
ACT   TCT   CCT   GCT   ATT   TTT   CTT   GTT
ACG   TCG   CCG   GCG   ATG   TTG   CTG   GTG
```

Software Analysis

All MegaBACE traces were analysed by in-house developed software and the resulting datasets of the HindIII+0/

MseI+0 individual fingerprints were processed by FPC software (Soderlund et al. vide supra) The HiindIII+2/MseI+3 AFLP fingerprints of the pooled BAC DNAs and the donor-parents of the genetic mapping population were also analysed by in-house software. The link of the HindIII+2/MseI+3 fragment to the HindIII+0/MseI+0 fragment in the corresponding individual BAC fingerprint was made in silico by searching fragments of comparable length within a certain error margin. The contigs were generated with a cut-off parameter set at various values between $10^{-7}$ and $10^{-14}$ and the resulting contig evaluated. Tolerance was set at 2-4. (i.e. 0.2-0.4 basepairs)

RESULTS AND CONCLUSIONS

Genetic markers have been linked to BAC contigs in a very efficient way and multiple genetic markers have been combined into an integrated physical and genetic map. The concept is applicable to different species with varying genome sizes with success, and without prior knowledge of the specific genomic sequence. The method provides for the effective integration of physical and genetic maps and will have an important impact in the genomic arena.

---

The invention claimed is:

1. A method for providing an integrated genetic and physical map of a genome or a part thereof, the method comprising the steps of:

(a) providing at least two individual genetic markers for the genome or a part thereof in the form of a genetic map;

(b) identifying at least one AFLP fragment characterizing each genetic marker by means of AFLP fingerprinting, employing at least one forward AFLP primer and at least one reverse AFLP primer;

(c) providing a library of clones comprising fragments of the genome or a part thereof, which is an artificial chromosome library;

(d) pooling individual clones in the library to generate a multitude of pools, each pool containing a multitude of individual clones from the library;

(e) generating an AFLP fingerprint for each of the pools employing forward AFLP primers and reverse AFLP primers;

(f) identifying in the multitude of pools a pool in which an AFLP fragment that was identified in step (b) is present in the fingerprint of the pool;

(g) generating an AFLP fingerprint for each of the individual clones in the pool identified in step (f) employing forward AFLP primers and reverse AFLP primers, and identifying the clone containing the AFLP fragment identified in step (b) in such clone's AFLP fingerprint;

(h) aligning the individual clone identified in step (g) to generate a contig;

(i) repeating steps (f)-(h) for at least a second AFLP fragment identified in step (b) whereby the second, or a further, AFLP fragment characterizes a second, or a further, genetic marker; and, (j) linking at least two contigs obtained in step (h);

thereby obtaining said integrated genetic and physical map of the genome or a part thereof, which comprises at least two genetic markers; wherein:

(1) the forward AFLP primers used in steps (b) and (e) comprise K selective nucleotides at the 3'-end, (2) the reverse AFLP primers used in steps (b) and (e) comprise L selective nucleotides at the 3'-end, (3) the forward AFLP primers used in step (g) comprise M selective nucleotides at the 3'-end, and (4) the reverse AFLP primers used in step (g) comprise N selective nucleotides at the 3' end, and wherein K, L, M, N are integers with a value from 0 to 10, and wherein the forward and reverse AFLP primers used in steps (b) and (e) are of higher selectivity, and the forward and reverse AFLP primers used in step (g) are of lower selectivity.

2. The method according to claim 1, wherein the AFLP primers used in steps (b) and (e) have in total at least 2 more selective nucleotides than the AFLP primers used in step (g).

3. The method according to claim 2, wherein the AFLP primers of lower selectivity have at least 0 selective nucleotides.

4. The method according to claim 2, wherein the AFLP primers of lower selectivity have at least 1 selective nucleotide.

5. The method according to claim 2, wherein the AFLP primers of lower selectivity have at least 2 selective nucleotides.

6. The method according to claim 2, wherein the AFLP primers of lower selectivity have at least 3 selective nucleotides.

7. The method according to claim 3, wherein each pool contains at most 0.6 genome equivalents of the total genome being analyzed.

8. The method according to claim 3, wherein each pool contains at most 0.5 genome equivalents of the total genome being analyzed.

9. The method according to claim 3, wherein each pool contains at most 0.3 genome equivalents of the total genome being analyzed.

10. The method according to claim 7, further comprising an additional pooling step.

11. The method according to claim 10, wherein the genetic markers are provided with a density of at least one genetic marker per 100 kb.

12. The method according to claim 11, wherein the contigs are generated using a computer program suitable for said aligning.

13. The method according to claim 12, wherein the artificial chromosome library contains at least 5 genome equivalents.

14. The method according to claim 12 wherein the computer program is FPC.

15. The method according to claim 1, wherein the artificial chromosome library is a BAC library or a YAC library.

16. The method according to claim 1, wherein the AFLP primers used in steps (b) and (e) have in total sum at least 3 more selective nucleotides than the AFLP primers used in step (g).

17. The method according to claim 1, wherein the AFLP primers used in steps (b) and (e) have in total at least 4 selective nucleotides than the AFLP primers used in step (g).

18. A method for linking a genetic marker to a physical marker in a genome or a part thereof, the method comprising the steps of:
(a) characterizing the genetic marker by means of at least one AFLP fragment identified through AFLP fingerprinting employing at least one forward AFLP primer and at least one reverse AFLP primer;
(b) providing a library of clones comprising fragments of the genome or a part thereof which is an artificial chromosome library;
(c) pooling individual clones in the library to generate a multitude of pools, each pool containing a multitude of individual clones from the library;
(d) generating an AFLP fingerprint for each of the pools employing forward AFLP primers and reverse AFLP primers;
(e) identifying in the multitude of pools a pool in which an AFLP fragment identified in step (a) is present in the fingerprint of the pool;
(f) generating an AFLP fingerprint for each of the individual clones in the pool identified in (e) employing forward AFLP primers and reverse AFLP primers, and identifying the clone containing the AFLP fragment identified in (a) in its AFLP fingerprint;
(g) aligning the individual clone identified in step (f) to generate a contig,
thereby linking the genetic marker to a physical marker; wherein
(1) the forward AFLP primers used in steps (a) and (d) comprise K selective nucleotides at the 3'-end,
(2) the reverse AFLP primers used in steps (a) and (d) comprise L selective nucleotides at the 3'-end,
(3) the forward AFLP primers used in step (f) comprise M selective nucleotides at the 3'-end, and
(4) the reverse AFLP primers used in step (f) comprise N selective nucleotides at the 3' end, and
wherein K, L, M, N are integers with a value from 0 to 10, and wherein the forward and reverse AFLP primers used in steps (b) and (e) are of higher selectivity, and the forward and reverse AFLP primers used in step (g) are of lower selectivity.

19. The method according to claim 18, wherein steps (a)-(g) are repeated for additional genetic markers in the genome or a part thereof and wherein the contigs obtained in (g) are aligned to obtain an integrated physical and genetic map.

20. The method according to claim 18, wherein the artificial chromosome library is a BAC library or a YAC library.

* * * * *

```
                         SEQUENCE LISTING

<160> NUMBER OF SEQ ID NOS: 8

<210> SEQ ID NO 1
<211> LENGTH: 17
<212> TYPE: DNA
<213> ORGANISM: Artificial
<220> FEATURE:
<223> OTHER INFORMATION: synthetic

<400> SEQUENCE: 1
ctcgtagact gcgtacc                                                       17

<210> SEQ ID NO 2
<211> LENGTH: 18
<212> TYPE: DNA
<213> ORGANISM: Artificial
<220> FEATURE:
<223> OTHER INFORMATION: synthetic

<400> SEQUENCE: 2
agctggtacg cagtctac                                                      18

<210> SEQ ID NO 3
<211> LENGTH: 16
<212> TYPE: DNA
<213> ORGANISM: Artificial
<220> FEATURE:
<223> OTHER INFORMATION: synthetic

<400> SEQUENCE: 3
gacgatgagt cctgag                                                        16

<210> SEQ ID NO 4
<211> LENGTH: 14
<212> TYPE: DNA
<213> ORGANISM: Artificial
<220> FEATURE:
<223> OTHER INFORMATION: synthetic

<400> SEQUENCE: 4
tactcaggac tcat                                                          14

<210> SEQ ID NO 5
<211> LENGTH: 16
<212> TYPE: DNA
<213> ORGANISM: Artificial
<220> FEATURE:
<223> OTHER INFORMATION: synthetic

<400> SEQUENCE: 5
gactgcgtac cagctt                                                        16
```

```
<210> SEQ ID NO 6
<211> LENGTH: 16
<212> TYPE: DNA
<213> ORGANISM: Artificial
<220> FEATURE:
<223> OTHER INFORMATION: synthetic

<400> SEQUENCE: 6
gatgagtcct gagtaa                                                      16

<210> SEQ ID NO 7
<211> LENGTH: 16
<212> TYPE: DNA
<213> ORGANISM: Artificial
<220> FEATURE:
<223> OTHER INFORMATION: synthetic

<400> SEQUENCE: 7
gactgcgtac cagctt                                                      16

<210> SEQ ID NO 8
<211> LENGTH: 16
<212> TYPE: DNA
<213> ORGANISM: Artificial
<220> FEATURE:
<223> OTHER INFORMATION: synthetic

<400> SEQUENCE: 8
gatgagtcct gagtaa                                                      16
```